United States Patent [19]

Stephens et al.

[11] 3,972,682
[45] Aug. 3, 1976

[54] PYROLYSIS FURNACE

[75] Inventors: Thomas M. Stephens, Menlo Park; Yoshihiro Takahashi, San Francisco, both of Calif.

[73] Assignee: Envirotech Corporation, Menlo Park, Calif.

[22] Filed: Oct. 6, 1975

[21] Appl. No.: 619,768

[52] U.S. Cl. ............................ 23/253 PC; 219/390
[51] Int. Cl.² .................... F27B 5/14; G01N 31/12
[58] Field of Search ................. 23/253 PC, 230 PC; 219/390

[56] References Cited
UNITED STATES PATENTS

| | | | |
|---|---|---|---|
| 2,964,389 | 12/1960 | Bennett et al. | 23/253 PC |
| 3,544,277 | 12/1970 | Lysyj et al. | 23/253 PC |
| 3,864,978 | 2/1975 | Stephens | 23/253 PC X |
| 3,926,562 | 12/1975 | Williams et al. | 23/230 PC X |

*Primary Examiner*—Robert M. Reese
*Attorney, Agent, or Firm*—Robert E. Krebs; Thomas S. MacDonald

[57] ABSTRACT

A furnace assembly for use in a chemical analysis system utilizing high-temperature pyrolytic techniques includes a refractory tube which defines a heated chamber wherein samples are pyrolyzed, inlet and outlet cap members mounted on opposite ends of the refractory tube, a cylindrical heating assembly which spacedly surrounds the refractory tube, and a frame which fixedly supports both the refractory tube and the heating assembly in a vertical orientation. The frame includes a stationary mounting plate and at least two rod-like members which fixedly extend in parallel downward from the stationary plate on opposite sides of the heating assembly. The heating assembly is fixed to the rods and a springy plate member is fixedly connected between the rods to provide a support upon which the outlet cap member rests and to press upwardly against the refractory tube when the same elongates during heating so that the upper and lower cap members are forceably sealed against the respective ends of the refractory tube.

8 Claims, 2 Drawing Figures

PYROLYSIS FURNACE

BACKGROUND OF THE INVENTION

1. Field of the Invention

The present invention generally relates to a furnace assembly for use in chemical analysis systems and, more particularly to a tubular-type furnace assembly for use in analysis systems utilizing high-temperature pyrolytic techniques.

2. State of the Art

In the field of analytical chemistry, high-temperature pyrolytic techniques are well known for deriving carbonaceous gases and vapors from small samples of liquids or solids by means of "cracking" carbonaceous molecular compounds in the samples by the application of heat. Once formed in a pyrolysis furnace, the gases and vapors can be passed into a detector or otherwise operated upon for analysis. For example, a conventional infrared analyzer may be utilized to determine the carbon-dioxide content of the volatilized gases and that determination may, in turn, be utilized as a measure of the organic carbon content of the initial sample. As another example, a microcoulometric analysis may be made of the volatilized gases.

Usually it is important that pyrolysis be accomplished in a sealed system so that extraneous gases and vapors do not contaminate the volatilized products. However, since typical pyrolysis temperatures reach as high as 1200°C, thermal expansions make it difficult to effectuate reliable gas-tight seals, especially in the pyrolysis furnace. Sealing compounds, for instance, usually cannot endure such high temperatures for prolonged periods. Also, it is difficult at such temperatures to seal materials to one another when the materials have different thermal expansion properties.

OBJECTS OF THE INVENTION

A primary object of the present invention is to provide an improved furnace for use in chemical analysis systems using high-temperature pyrolytic techniques.

A more specific object is to provide an improved sealing and mounting arrangement for a tubular-type high-temperature pyrolysis furnace.

BRIEF DESCRIPTION OF THE DRAWINGS

The aforementioned and other objects and advantages of the present invention may be readily ascertained by reference to the following description and appended drawings which are offered by way of illustration only and not in limitation of the invention, the scope as defined by the appended claims and equivalents to the structure and material set forth hereinafter.

In the drawings.

DETAILED DESCRIPTION OF THE PREFERRED EMBODIMENT

Figure 1:
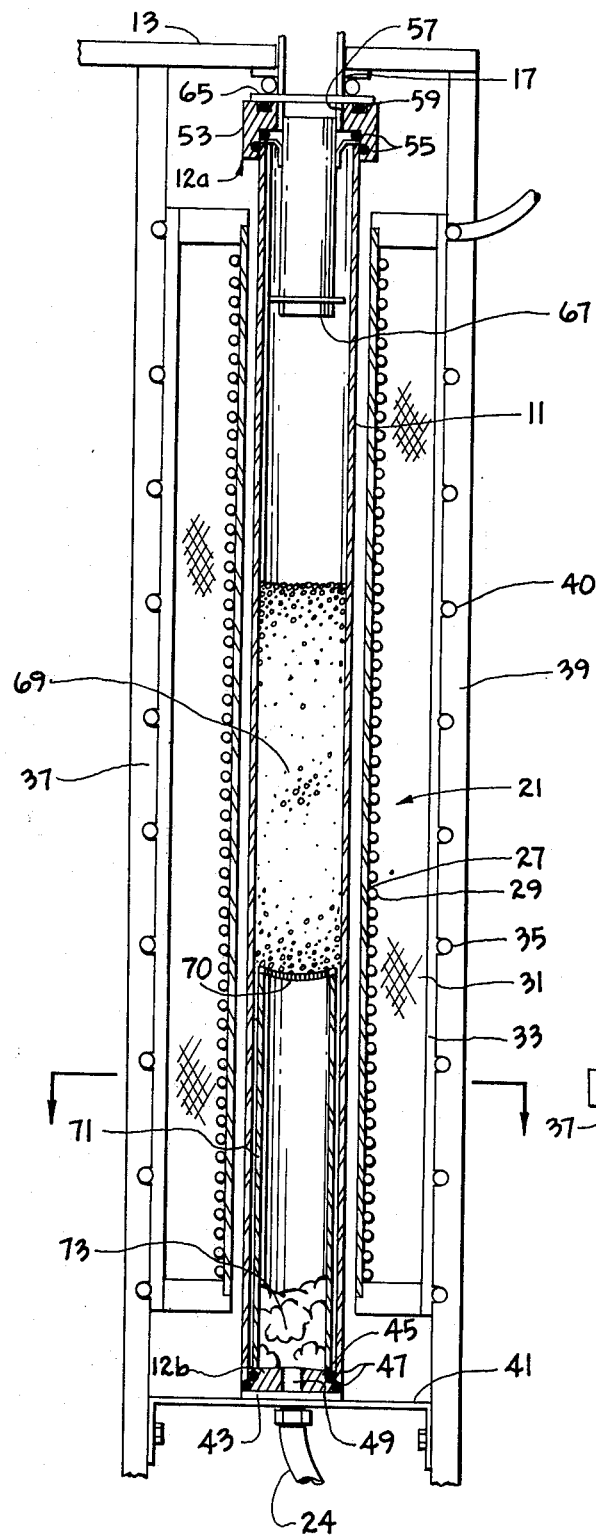
FIG. 1 is a side elevation in section of a pyrolysis furnace assembly according to the present invention.
Figure 2:
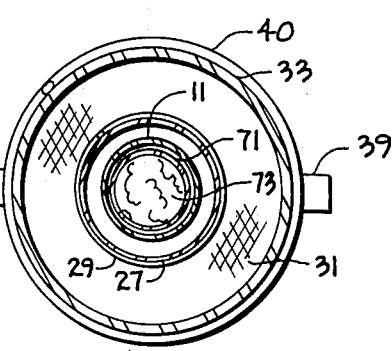
FIG. 2 is a sectional view taken along the lines 2—2 in FIG. 1 for viewing in the direction of the arrows.

The furnace assembly according to our invention includes a straight, vertically-disposed refractory tube 11 of generally circular cross-section which defines a chamber wherein liquid or solid samples are pyrolyzed. The upper and lower ends of the refractory tube have squared edges and those ends are sealingly closed by end caps 12a and 12b, respectively, which will be described in detail later herein. The refractory tube 11 can be made from materials such as ceramic, glass, quartz or from metals or metallic compounds with high melting points; in practice, we usually use alumina. Above the refractory tube is a stationary plate 13 whereon is mounted a sampling device, not shown, for ejecting aliquot samples downwardly into the refractory tube via an inlet conduit 17 that is in sealed communication with the upper end cap 12a of the refractory tube 11. The sample injection device may, for example, comprise a valve as shown in U.S. Pat. No. 3,864,978 to Thomas M. Stephens. Spacedly surrounding the refractory tube 11 is a heating assembly 21 of generally cylindrical configuration. In sealed communication with the lower end cap 12b is an outlet conduit 24 through which pyrolyzed gases and vapors are discharged from the refractory tube 11.

Mounted concentrically within the upper end of the refractory tube 11 is a short open-ended tubular member 67 made of a material such as Hastaloy which has relatively poor heat conducting characteristics. The purpose of this member, which becomes very hot when the furnace is in operation, is to assure the vaporization of any sample materials which contact it. Disposed within the refractory tube 11 at a substantial distance below the lower end of the tubular member 67 is a catalytic bed or packing 69 which is constructed of a compacted fibrous or granular material essentially chemically inert to oxygen and steam. "Essentially chemically inert" means the material adopts an essentially constant chemical consistency upon exposure to steam and oxygen, at an elevated combustion supporting temperature, except that it is contemplated herein that the surface of such material may adsorb or desorb gases such as oxygen. Suitable materials of construction for the diffusing member include quartz wool, quartz chips, sand, pumice, and the like siliceous materials. Also suitable are finely divided transition metals, e.g., nickel chrome, manganese and platinum, and transition metal oxides, e.g., copper, cobalt, manganese, vanadium, cerium and thorium oxides. The packing 69 is supported at an intermediate position within the refractory tube 11 by a perforate plate 70 which, in the illustrated embodiment, is fixed atop a supporting cylindrical member 71 with a hollow interior. The interior of the cylindrical member 71 can be utilized to collect sodium-chloride as, for example, when sea water samples are being analyzed. Disposed within the lower end of the refractory tube 11 is a permeable plug 73 of quartz wool or the like to assure complete mixing and filtering of the pyrolyzed gases and vapors prior to their exiting the furnace assembly.

The aforementioned heating assembly 21 will now be further described. Preferably, it includes a thin tubular shell 27 whose inside diameter exceeds the outside diameter of the refractory tube 11, say by about one-quarter inch, which is mounted to concentrically surround the refractory tube. In practice, we usually make the tubular shell 27 from a heat-conducting refractory material such as mullite or ceramic. Wound about the tubular shell 27 is a continuous electric heating coil 29 which is coupled to a conventional power source, not shown. The heating coil 29 is embedded in an insulating cylinder 31, made of asbestos for example, which surrounds the tubular shell 27. Surrounding the insulating cylinder 31 is a cylindrical heat-conducting sheath 33 formed of metal, for example. Encircling the heat-conducting sheath 33 is a coiled tube 35 which is in communication with a source of cooling liquid, such as water, that is forced through the coil to cool the surface of the sheath 33 to a temperature safe to the touch.

The refractory tube 11 and the heating assembly 21 are both fixedly supported in a generally vertically-disposed position by a frame that extends from below the stationary mounting plate 13. In the illustrated embodiment, the frame includes two vertical rods 37 and 39 which are rigidly connected at their upper ends to the stationary mounting plate 13 and which extend downward therefrom the length of the refractory tube 11. (Clearly, more than two vertical rods could comprise the furnace frame, but only two were shown for purposes of clarity.) The sheath 33 of the heating assembly 21 is fixed directly to the rods, and grooves 40 are formed therein through which the cooling tube 35 passes as it coils about the sheath 33. A thin, springy plate 41 fixedly extends between the lower ends of the rods 37 and 39, and the lower end cap 12b of the refractory tube rests upon that plate.

In the illustrated embodiment, the lower end cap 12b comprises a circular member which has a radially extending rim portion 43 that engages the end edge of the refractory tube 11 and a cylindrical plug-like portion 45 that fits into the end of the refractory tube. O-ring grooves are formed in the periphery of the plug-like portion and O-rings 47 are fitted thereinto to press against the inside wall and the end edge of the refractory tube 11. Preferably, the O-rings are made of Viton or are Teflon coated. An aperture 49 is formed centrally through the cap 12b and the aforementioned outlet conduit 24 is sealingly received therein.

The upper end cap 12a comprises, in the illustrated embodiment, a circular member having an integral peripheral annular rim 53 that fits about the upper end of the refractory tube 11. O-ring grooves are formed in the inside face of the annular rim 53 and O-rings 55 are fitted thereinto to press against the outside wall and the end edge of the refractory tube 11. An aperture 57 is formed centrally through the cap 12 and the aforementioned inlet conduit 17 is sealingly received therein. An O-ring groove 59 is formed in the upper surface of the cap 12a about the central aperture 57 and an O-ring is also fitted into that groove to press against the lower face of an overlying stationary annular member 65 mounted on the inlet conduit 17.

In the assemblage, the spring plate 41 presses the refractory tube 11 upwardly toward the stationary mounting plate 13 and thereby forces the end cap members 12a and 12b against the ends of the refractory tube 11. To further assist sealing, the end edges of the refractory tube should be squared, but the exact length of the refractory tube is not critical since the plate 41 can flex somewhat. In operation of the furnace, the springy plate 41 flexes downwardly as the refractory tube elongates during heating. (Typically, the expansion is about three/sixteenth inch.) At some point during such thermal expansion, the opposite end edges of the refractory tube seal against the adjacent O-rings 47 and 59. In fact, we normally rely solely on such thermal expansion of the refractory tube to make the seal and do not establish a sealed relationship between the refractory tube and its end caps when the furnace is cold. Although the upward pressure on the refractory tube increases somewhat as the plate 41 flexes, we have found that such pressure will not cause fracture or cracking of the refractory tube, yet will maintain the integrity of the seals.

We claim:
1. A furnace assembly for use in a chemical analysis system utilizing high-temperature pyrolytic techniques comprising:
   a. a straight refractory tube which defines a heated chamber wherein samples are pyrolyzed and which has an inlet end and an outlet end with generally square end edges;
   b. inlet and outlet cap members mounted on said inlet and outlet end edges, respectively, of said refractory tube;
   c. a heating assembly of generally cylindrical configuration spacedly surrounding said refractory tube;
   d. a frame fixedly supporting said refractory tube and said heating assembly in a vertically-disposed position, said frame means comprising a stationary mounting member and at least two rod-like members which fixedly extend in parallel downward from said stationary mounting member on opposite sides of said cylindrical heating assembly, said heating assembly being fixed to said rods; and
   e. a means which extends transversely between said rod-like members to provide a support upon which the outlet cap member rests and which presses said cap members to seal against said end edges of said refractory tube as said refractory tube expands longitudinally upon the application of heat by said heating assembly.

2. A furnace assembly according to claim 1 wherein a short open-ended tubular member is mounted concentrically within the upper end of said refractory tube, which member is made of a material having relatively poor heat conducting characteristics.

3. A furnace assembly for use in a chemical analysis system utilizing high-temperature pyrolytic techniques comprising:
   a. a straight refractory tube which defines a heated chamber wherein samples are pyrolyzed and which has an inlet end and an outlet end with generally squared end edges;
   b. inlet and outlet cap members mounted on said inlet and outlet end edges, respectively, of said refractory tube;
   c. a heating assembly of generally cylindrical configuration spacedly surrounding said refractory tube and coupled to a power supply to heat the interior of said refractory tube; and
   d. a frame means fixedly supporting said refractory tube and said heating assembly in a vertically-disposed position, said frame means comprising a stationary mounting member and at least two rod-like members which fixedly extend in parallel downward from said stationary mounting member on opposite sides of said cylindrical heating assembly, said heating assembly being fixed to said rods; said frame means further comprising a springy, plate member which fixedly extends transversely between said rod-like members to provide a support upon which said outlet cap member rests and which presses upwardly against said refractory tube when said refractory tube is heated so that said upper and lower cap members are forceably sealed against the respective end edges of said refractory tube.

4. A furnace assembly according to claim 3 further including O-ring members mounted within said inlet and outlet cap members to engage said inlet and outlet end edges of said refractory tube.

5. A furnace assembly according to claim 3 wherein said inlet cap member has an aperture formed centrally therein to sealingly receive an inlet conduit and said outlet cap member also has an aperture formed centrally therein to sealingly receive an outlet conduit.

6. A furnace assembly according to claim 3 wherein said inlet and outlet cap members each include a radially extending rim portion which fits against the associated respective end edge of said refractory tube.

7. A furnace assembly according to claim 3 wherein a short open-ended tubular member is mounted concentrically within the upper end of said refractory tube, which member is made of a material having relatively poor heat conducting characteristics.

8. A furnace assembly according to claim 7 wherein a catalytic bed is supported within said refractory tube at a position spaced from the outlet end thereof and there is a void space within said refractory tube toward said outlet end.

* * * * *

UNITED STATES PATENT AND TRADEMARK OFFICE
CERTIFICATE OF CORRECTION

PATENT NO. : 3,972,682
DATED : AUGUST 3, 1976
INVENTOR(S) : THOMAS M. STEPHENS ET AL

It is certified that error appears in the above–identified patent and that said Letters Patent are hereby corrected as shown below:

In Column 4, line 16, after "frame" insert --means--.

Signed and Sealed this

Fifteenth Day of January 1980

[SEAL]

Attest:

SIDNEY A. DIAMOND

Attesting Officer

Commissioner of Patents and Trademarks